US011737727B2

(12) United States Patent
Onodera et al.

(10) Patent No.: US 11,737,727 B2
(45) Date of Patent: Aug. 29, 2023

(54) ULTRASONIC DIAGNOSTIC APPARATUS

(71) Applicant: CANON MEDICAL SYSTEMS CORPORATION, Otawara (JP)

(72) Inventors: Hideo Onodera, Nasushiobara (JP); Shingo Toyoda, Utsunomiya (JP); Shinichiro Kikuchi, Otawara (JP); Shuta Fujiwara, Nasushiobara (JP); Yuji Kuwana, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 310 days.

(21) Appl. No.: 17/063,835

(22) Filed: Oct. 6, 2020

(65) Prior Publication Data

US 2021/0100529 A1  Apr. 8, 2021

(30) Foreign Application Priority Data

Oct. 7, 2019 (JP) .................................. 2019-184462

(51) Int. Cl.
| | |
|---|---|
| *A61B 8/00* | (2006.01) |
| *A61B 8/08* | (2006.01) |
| *F16M 11/42* | (2006.01) |
| *B60B 1/00* | (2006.01) |
| *B62B 1/00* | (2006.01) |
| *F16M 11/24* | (2006.01) |

(52) U.S. Cl.
CPC .......... *A61B 8/4405* (2013.01); *A61B 8/4209* (2013.01); *A61B 8/4427* (2013.01); *A61B 8/5207* (2013.01); *A61B 8/56* (2013.01); *A61B 8/54* (2013.01); *B60B 1/00* (2013.01); *B62B 1/00* (2013.01); *F16M 11/24* (2013.01); *F16M 11/42* (2013.01)

(58) Field of Classification Search
CPC ..... A61B 8/4405; A61B 8/4444; A61B 8/483; A61B 8/461; A61B 8/565; A61B 8/4477; A61B 8/4427; A61B 8/5207; A61B 8/56; A61B 8/4411; A61B 8/4472; B60B 1/00; B62B 1/00; F16M 11/24; F16M 11/42
See application file for complete search history.

(56) References Cited

U.S. PATENT DOCUMENTS

| | | | | |
|---|---|---|---|---|
| 2006/0158050 | A1* | 7/2006 | Maeda | ...................... H02K 7/14 |
| | | | | 310/58 |
| 2016/0183920 | A1* | 6/2016 | Woo | ....................... A61B 8/461 |
| | | | | 600/440 |

FOREIGN PATENT DOCUMENTS

| | | | |
|---|---|---|---|
| CN | 209863880 U | * 12/2019 | |
| EP | 3329855 A1 | * 6/2018 | ........... A61B 8/4405 |

(Continued)

OTHER PUBLICATIONS

Office Action dated March 28, 2023 in Japanese Patent Application No. 2019-184462, 4 pages.

*Primary Examiner* — Tan Le
(74) *Attorney, Agent, or Firm* — Oblon, McClelland, Maier & Neustadt, L.L.P.

(57) ABSTRACT

An ultrasonic diagnostic apparatus according to an embodiment includes a body, a plurality of wheels, and control circuitry. The body sends and receives ultrasonic waves to generate an ultrasonic image. The plurality of wheels supports and moves the body. The assist wheel is electrically driven, and assists movement of the body. The control circuitry is configured to control switching between grounded and ungrounded of the assist wheel to a floor.

13 Claims, 7 Drawing Sheets

(56) References Cited

FOREIGN PATENT DOCUMENTS

| JP | 10-129497 A | 5/1998 | |
|----|----|----|----|
| JP | 11-146508 A | 5/1999 | |
| JP | 2009-119954 A | 6/2009 | |
| JP | 2016-088115 A | 5/2016 | |
| JP | 2019-151247 A | 9/2019 | |
| WO | WO-2006111874 A2 * | 10/2006 | ............... A61B 8/08 |
| WO | WO 2015/107964 A1 | 7/2015 | |

* cited by examiner

ULTRASONIC DIAGNOSTIC APPARATUS

CROSS-REFERENCE TO RELATED APPLICATIONS

This application claims the benefit of priority of Japanese Patent Application No. 2019-184462, filed Oct. 7, 2019, the entire contents of which are incorporated herein by reference.

FIELD

Embodiments described herein relate generally to an ultrasonic diagnostic apparatus.

BACKGROUND

The ultrasonic diagnostic apparatus is used not only in a dedicated examination room but also in a plurality of rooms in a hospital such as an examination room, a hospital room, and an operating room. For example, when using an ultrasonic diagnostic device in an inpatient ward, the user moves the ultrasonic diagnostic apparatus used in a room to another room where the next patient is to be examined. Therefore, the ultrasonic diagnostic apparatus is provided with moving means such as casters and handlebars on the main body.

Recently, the size and weight of the ultrasonic diagnostic apparatuses have been reduced. However, many ultrasonic diagnostic apparatuses are still heavy that is difficult for the user to lift up, and thus, moving the ultrasonic diagnostic apparatus is a burden on the user.

DETAILED DESCRIPTION

Hereinbelow, a description will be given of an ultrasonic diagnostic apparatus according to embodiments with reference to the drawings.

An ultrasonic diagnostic apparatus according to an embodiment includes a body, a plurality of wheels, and control circuitry. The body sends and receives ultrasonic waves to generate an ultrasonic image. The plurality of wheels supports and moves the body. The assist wheel is electrically driven, and assists movement of the body. The control circuitry is configured to control switching between grounded and ungrounded of the assist wheel to a floor.

(1) Configuration

Figure 1:
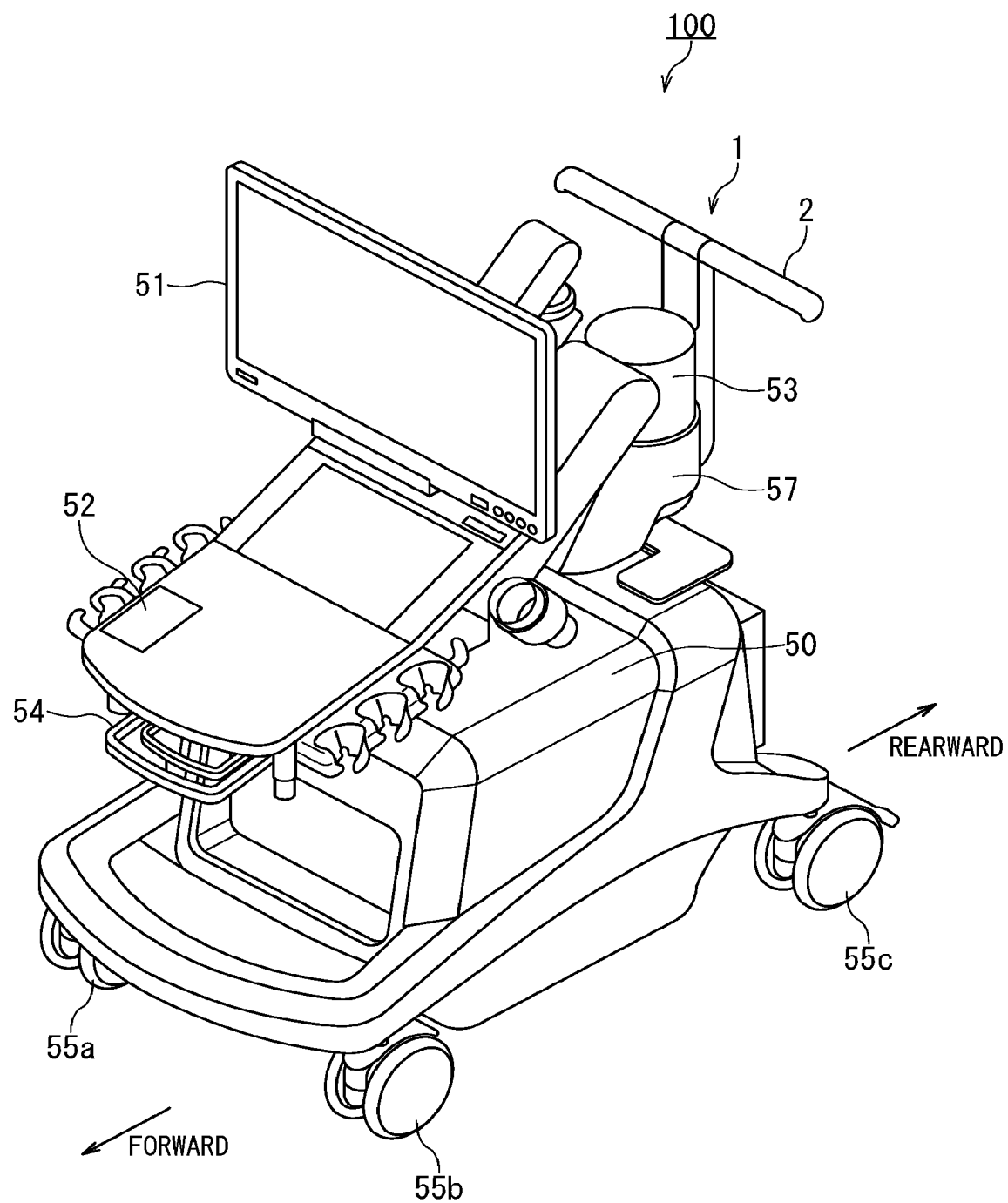
FIG. 1 is a perspective view of an ultrasonic diagnostic apparatus according to an embodiment.

FIG. 1 is a perspective view of the ultrasonic diagnostic apparatus 100 according to the embodiment. In the following description, the same reference numerals will be given to the equivalent configurations, and duplicate description will be omitted.

Figure 2:
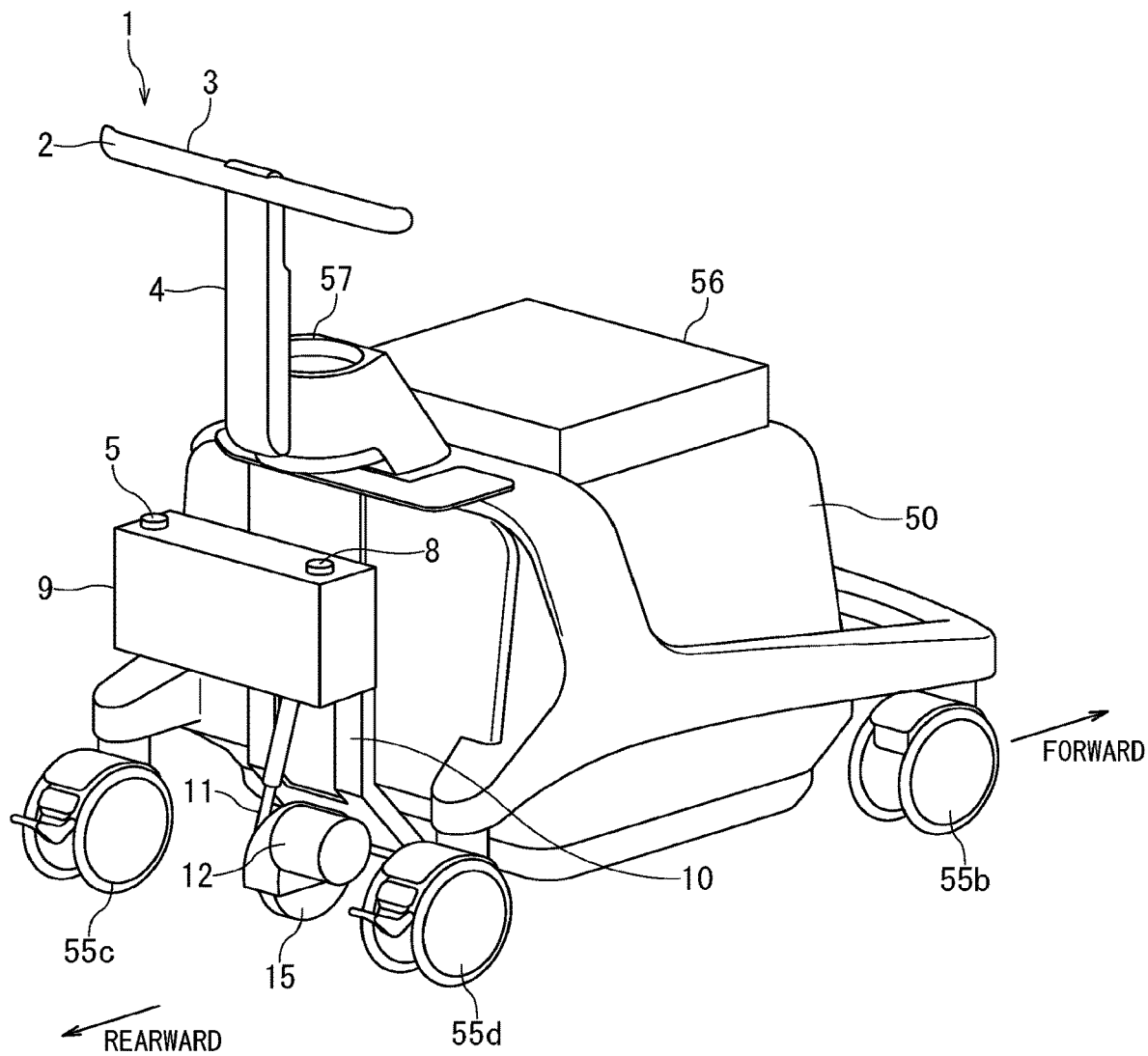
FIG. 2 is a perspective view of the ultrasonic diagnostic apparatus according to the embodiment as viewed from rearward.

As shown in FIG. 1, the ultrasonic diagnostic apparatus 100 includes a movement assist unit 1, a rear handlebar 2, a body 50, a display 51, an input interface 52, an arm 53, a front handlebar 54, a main wheel 55a, a main wheel 55b, a main wheel 55c, a main wheel 55d, a battery 56 (shown in FIG. 2, for example), and an arm mounting member 57. In the example of FIG. 1, the battery 56 shown in FIG. 2 is not shown for simplicity.

In the following description, as shown in FIG. 1, the side to which the front handlebar 54 is attached is defined as the "forward" of the ultrasonic diagnostic apparatus 100, and the side to which the rear handlebar 2 is attached is defined as the "rearward" of the ultrasonic diagnostic apparatus 100. Further, to move the ultrasonic diagnostic apparatus 100 forward is referred to as "forward travel", and to move it rearward is referred to as "reverse travel".

The body 50 includes a transmission circuit, a reception circuit, processing circuitry, and a memory. The body 50 transmits and receives ultrasonic waves via an ultrasonic probe (not shown) to generate ultrasonic images.

The transmission circuit includes, for example, a transmission signal forming circuit such as a trigger generation circuit, a delay circuit, and a pulser circuit, and supplies a drive signal to the ultrasonic probe. The trigger generation circuit repeatedly generates rate pulses at a predetermined rate frequency. The delay circuit is a circuit that delays the rate pulse by a predetermined delay amount for each oscillating element of the ultrasonic probe, and is a circuit for focusing the transmitted beam and directing it in a desired direction. The pulser circuit generates a pulse signal based on the delayed rate pulse and applies it to each oscillating element of the ultrasonic probe.

The reception circuit includes a received signal processing circuit including an amplifier circuit, an A/D conversion circuit, and a beam forming circuit. The reception circuit amplifies the analog received signal supplied from each oscillating element of the ultrasonic probe with the amplifier circuit, and then converts it into a digital signal with the A/D conversion circuit. After that, in the beam forming circuit, a delay amount is given to each oscillating element, and by adding them, a received signal corresponding to a desired beam direction is formed.

The processing circuitry includes a processor, for example. The processing circuitry realizes, for example, a signal processing function such as a B mode processing function and a color Doppler processing function, and a display control function. These functions are realized by the processor executing a program stored in the memory.

The B-mode processing function performs signal processing such as logarithmic amplification and envelope detection processing on ultrasonic data to generate data (B-mode data) in which the signal strength is expressed by luminance. In addition, the color Doppler processing function performs MTI (Moving Target Indication) processing on ultrasonic data, and then generates data (Doppler data) that extracts moving state information such as average speed, dispersion, and power for multiple points. The B-mode data and the Doppler data generated by these signal processes are stored in the memory.

The display control function controls displaying the B mode data and the Doppler data on the display 51. For example, the display control function generates ultrasonic images by performing scan conversion on the B mode data and the Doppler data. The display control function causes the display 51 to display the ultrasonic image and the data related to the ultrasonic image.

The memory is equipped with a configuration including a storage medium that can be read by a processor, such as a magnetic memory medium, an optical memory medium, and a semiconductor memory. The memory may be configured such that some or all of the program and data in those storage media can be downloaded by means of communication via an electronic network, or can be given via a portable storage medium such as an optical disk. A part or all of the information stored in the memory may be distributed and stored, or may be duplicated and stored, in at least one storage medium such as an external memory or a memory (not shown) of the body 50.

The display 51 is configured by a general display device such as a liquid crystal display or an OLED (Organic Light Emitting Diode) display, and displays an ultrasonic image under the control of a processing circuit.

The input interface 52 is composited of a general input device such as a trackball, a switch, a button, a mouse, a keyboard, a touch pad that performs an input operation by touching an operation surface, a non-contact input circuit using an optical sensor, a voice input circuit, and the like, and outputs an operation input signal corresponding to a user's operation to the processing circuitry.

The display 51 and the input interface 52 may be integrated to form a touch panel.

The arm 53 supports the display 51 and the input interface 52. Further, the arm 53 can change the positions of the display 51 and the input interface 52 to go up, down, left and right by rotating the display 51 and the input interface 52 in the azimuth direction and the elevation direction. Further, the display 51 and the input interface 52 are detachably attached to the body 50 via an arm mounting member 57 provided in the lower part of the arm 53.

The front handlebar 54 is a handle that the user grips when moving the ultrasonic diagnostic apparatus 100 when the user is on the forward side. Further, the front handlebar 54 may be used as a handle for moving the display 51 and the input interface 52 supported via the arm 53 up, down, left and right.

The main wheels 55*a*, 55*b*, 55*c*, 55*d* support the body 50 and move the body 50. The main wheels 55*a* and 55*b* are front wheels, and the main wheels 55*c* and 55*d* are rear wheels. The main wheels 55*a* to 55*d* can freely rotate around each mounting axis of each of the main wheels 55*a* to 55*d* with respect to the body 50 to move the body 50 360 degrees in any direction. Since the main wheels 55*a* to 55*d* may have the same configuration as the conventional one, detailed description thereof will be omitted here.

The battery 56 is a storage battery that supplies electric power to the ultrasonic diagnostic apparatus 100. The battery 56 may be charged with the electric power acquired by the body 50 from a commercial power supply via an AC power adapter, or may be detached from the body 50 and charged with a dedicated charger.

The movement assist unit 1 assists the movement of the ultrasonic diagnostic apparatus 100 when the rear handlebar 2 is operated to move the ultrasonic diagnostic apparatus 100 when the user is on the rearward side. The movement assist unit 1 and the rear handlebar 2 will be described in detail with reference to FIGS. 2 and 3.

FIG. 2 is a perspective view of the ultrasonic diagnostic apparatus 100 according to the embodiment as viewed from rearward. As shown in FIG. 2, the movement assist unit 1 of the ultrasonic diagnostic apparatus 100 according to the embodiment is attached to the rearward of the ultrasonic diagnostic apparatus 100. In FIG. 2, the display 51, the input interface 52, the arm 53, and the front handlebar 54 are not shown.

Figure 3:
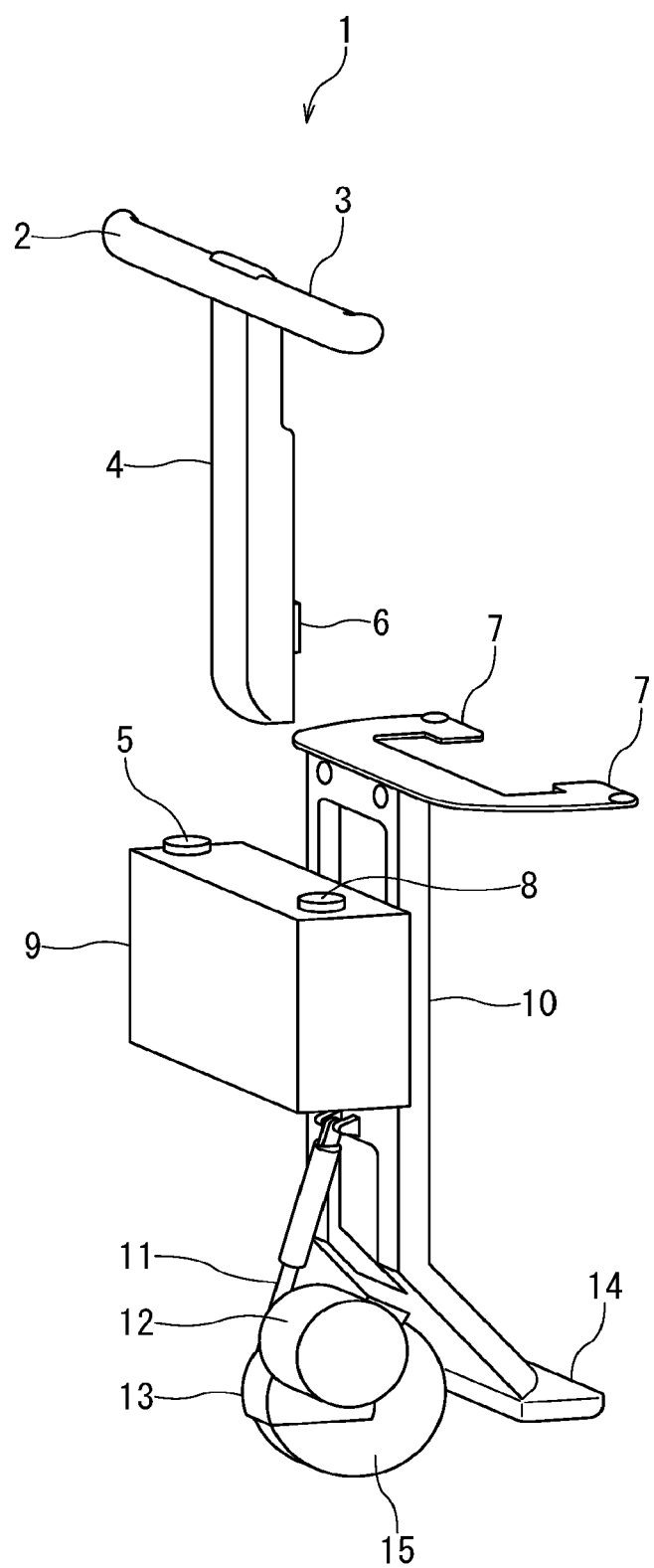
FIG. 3 is a perspective view schematically showing a movement assist unit detached from the ultrasonic diagnostic apparatus.

FIG. 3 is a perspective view schematically showing the movement assist unit 1 detached from the ultrasonic diagnostic apparatus 100.

In FIG. 2, an example is shown in which the battery 56 is provided on the top of the body 50, but the position where the battery 56 is provided is not limited to the example shown in FIG. 2. For example, the battery 56 may be provided on the side surface or the bottom surface of the body 50, or may be contained in the body 50.

As shown in FIGS. 2 and 3, the movement assist unit 1 includes a rear handlebar 2, a wheel elevating switch 3, a handle supporting member 4, an emergency stop switch 5, a sensor 6, an upper mounting portion 7, a power switch 8, a control device 9, a holding member 10, a wheel elevating device 11, a wheel assist device 12, a wheel cover 13, a lower mounting portion 14, and an assist wheel 15.

The rear handlebar 2 is a handle that is gripped and operated by the user when moving the ultrasonic diagnostic apparatus 100. The rear handlebar 2 is, for example, T-shaped or U-shaped. However, the shape of the rear handlebar 2 is not limited to a T-shape or a U-shape, and may be any shape as long as it is easy for the user to grip and operate.

The wheel elevating switch 3 is a switch for switching between grounded and ungrounded of the assist wheel 15. The wheel elevating switch 3 outputs the raising signal and the lowering signal of the assist wheel 15 to the control device 9. The wheel elevating switch 3 is, for example, a momentary switch provided on at least one of the grips on both sides of the rear handlebar 2. At the same time as the user grasps the grip of the rear handlebar 2, the wheel elevating switch 3 is pressed and turns on, and the assist wheel 15 lowers and touches the floor. The wheel elevating switch 3 may turn on only when the user holds the grip of the rear handlebar 2 for a certain period of time exceeding the threshold value.

At the same time as the user releases the grip of the rear handlebar 2, the wheel elevating switch 3 is released and turned off, and the assist wheel 15 raises and becomes ungrounded (that is, it moves off the floor). Further, for example, the wheel elevating switch 3 may be attached to the forward of the grip of the rear handlebar 2 so that the wheel elevating switch 3 is pressed by the finger of the user when the user grasps the rear handlebar 2. The mounting position of the wheel elevating switch 3 is not limited to the above example, and may be mounted at any position.

Further, the wheel elevating switch 3 may be provided at any position as long as it is easy for the user to operate when gripping the rear handlebar 2. For example, the wheel elevating switch 3 may be provided on the upper portion of the handle supporting member 4. Further, the example in which the wheel elevating switch 3 is pressed at the same time as gripping the rear handlebar 2 has been described in the above description, but the user may be able to press the wheel elevating switch 3 at an arbitrary timing. In this case, the wheel elevating switch 3 may be an alternate switch.

Still further, wheel elevating switch 3 is not limited to switches. For example, the wheel elevating switch 3 may be a touch sensor or a myoelectric sensor that detects that the user's palm touches the rear handlebar 2 or that the user's hand grips the rear handlebar 2.

The wheel elevating device 11 raises and lowers the assist wheel 15 to switch between grounded and ungrounded of the assist wheel 15 to the floor. The wheel elevating device 11 raises and lowers the wheel according to a command from the control device 9. The wheel elevating device 11 may include an electric cylinder 11. The wheel elevating device 11 is not limited to the electric cylinder 11, and may be any device as long as the assist wheel 15 can be switched between grounded and ungrounded.

The sensor 6 is provided on the handle supporting member 4, for example, and detects a load toward the forward-backward direction on the handle supporting member 4 when the user operates the rear handlebar 2. The sensor 6 is, for example, a distortion sensor but is not limited to the distortion sensor. The sensor 6 may be any sensor as long as it can detect the load when the user operates the rear handlebar 2 in the forward-rearward direction and output a signal corresponding to the magnitude of the detected load. For example, the sensor 6 may be configured by combining a pressure sensor and a spring to detect a load toward the forward-rearward direction.

Further, the sensor 6 may detect a load toward the forward-rearward direction on the handle supporting member 4 and may function as a wheel elevating switch 3. For example, when the sensor 6 is a myoelectric sensor, the grip of the rear handlebar 2 and the magnitude and direction of the force applied to the rear handlebar 2 can be detected at the same time. The sensor 6 may be omitted when the wheel elevating switch 3 also functions as the sensor 6.

The wheel assist device 12 is a drive device that rotates the assist wheel 15. The wheel assist device 12 may be an assist motor. The assist motor that drives the assist wheel 15 is driven by the electric power from the battery 56. The wheel assist device 12 rotates the assist wheel 15 in accordance with a command from the control device 9. When the ultrasonic diagnostic apparatus 100 goes down an inclined passage, the assist wheel 15 is rotated by the weight of the ultrasonic diagnostic apparatus 100, and the assist motor is rotated by this torque. In such a case, the battery 56 may be charged using the regenerative power generated from the assist motor. The wheel assist device 12 can be realized by various known methods as long as the wheel assist device 12 has a configuration in which power for rotating the assist wheel 15 can be applied to the assist wheel 15. The wheel assist device 12 may be provided inside the assist wheel 15.

The battery 56 may be used by the wheel assist device 12 and the body 50. That is, the battery 56 may supply power to both the wheel assist device 12 and the body 50.

The assist wheel 15 assists the movement of the body 50. The assist wheel 15 may be provided between the two rear wheels, i.e., the main wheels 55c and 55d. The center of rotation of the assist wheel 15 may be connected to the rotation shaft of the wheel assist device (assist motor) 12. The assist wheel 15 rotates forward and rearward by a driving force from the wheel assist device 12 via the rotation shaft, and assists the forward and rearward movement of the body 50.

The control device 9 includes a processor and a memory, and generally controls the movement assist unit 1. The configuration of the control device 9 will be described later in detail with reference to FIG. 5.

The holding member 10 holds components of the movement assist unit 1. Further, the holding member 10 houses wiring for connecting the control device 9 and each component of the movement assist unit 1.

The upper mounting portion 7 and the lower mounting portion 14 are provided on the holding member 10, and have a structure for attaching/detaching the movement assist unit 1 to/from the body 50. The upper mounting portion 7 is mounted on the base of the arm mounting member 57, and has a U-shape or a C-shape so as not to interfere with the arm mounting member 57.

The power switch 8 is the main power switch of the movement assist unit 1. When the power switch 8 is pressed, the power circuit 91 is supplied with power from the battery 56. The power circuit 91 will be described later in detail with reference to FIG. 5.

The emergency stop switch 5 is a switch that outputs an emergency stop signal to the power circuit 91. When the emergency stop switch 5 is pressed by the user, the power supply to the wheel assist device 12 is cut off.

Figure 4:
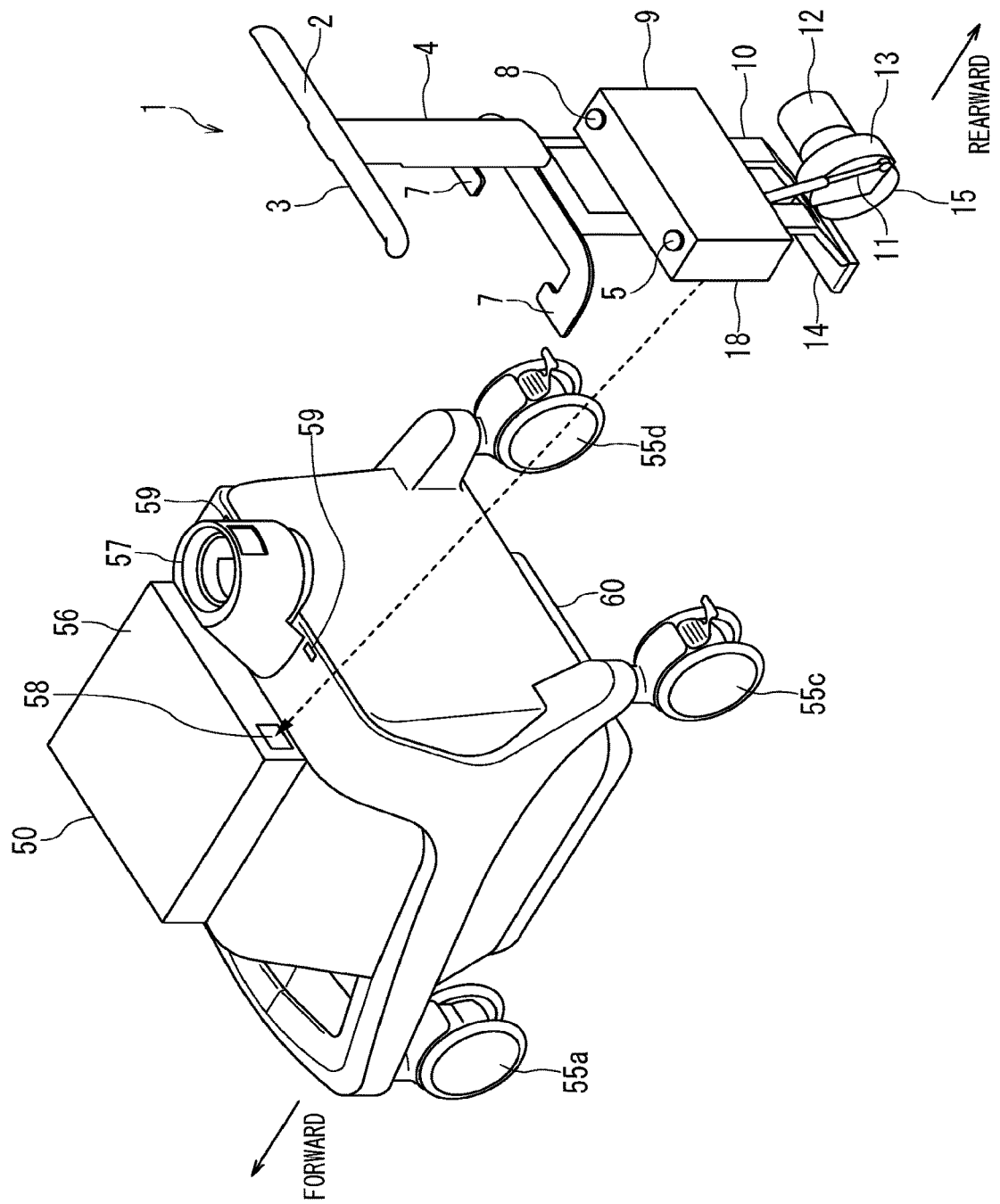
FIG. 4 is a schematic view showing an example of a method of attaching/detaching the movement assist unit to/from the body of the ultrasonic diagnostic apparatus according to the embodiment.

FIG. 4 is a schematic view showing an example of a method of attaching/detaching the movement assist unit 1 to/from the body 50 of the ultrasonic diagnostic apparatus 100 according to the embodiment.

The movement assist unit 1 is detachably attached to the body 50 at two or more sites. The movement assist unit 1 may be detachably attached to the body 50 with screws. Screw holes are provided in the upper mounting portion 7 of the movement assist unit 1 and the upper mounting portion 59 of the body 50, and both are screwed together by a screw. Similarly, screw holes are provided in the lower mounting portion 14 of the movement assist unit 1 and the lower mounting portion 60 of the body 50, and both are screwed together by a screw.

As long as the movement assist unit 1 is fixed so as not to come off from the body 50 when moving the ultrasonic diagnostic apparatus 100, the mounting method of the movement assist unit 1 is not limited.

The battery 56 is provided with a port 58 (terminal hole), and the control device 9 has a connector 18 (terminal) that can be connected to the port 58. By connecting the connector 18 of the movement assist unit 1 and the port 58 of the battery 56 to each other via, e.g. a dedicated power cable, power can be supplied from the battery 56 to the movement assist unit 1.

Although FIG. 4 shows an example in which the opening of the port 58 is provided so as to face the movement assist unit 1, the port 58 may be provided at any position on the battery 56 as long as the port 58 does not interfere with the use of the ultrasonic diagnostic apparatus 100 or the attachment of the movement assist unit 1. Similarly, the connector 18 may be provided at any position as long as the connector 18 does not interfere with the attachment of the movement assist unit 1.

Figure 5:
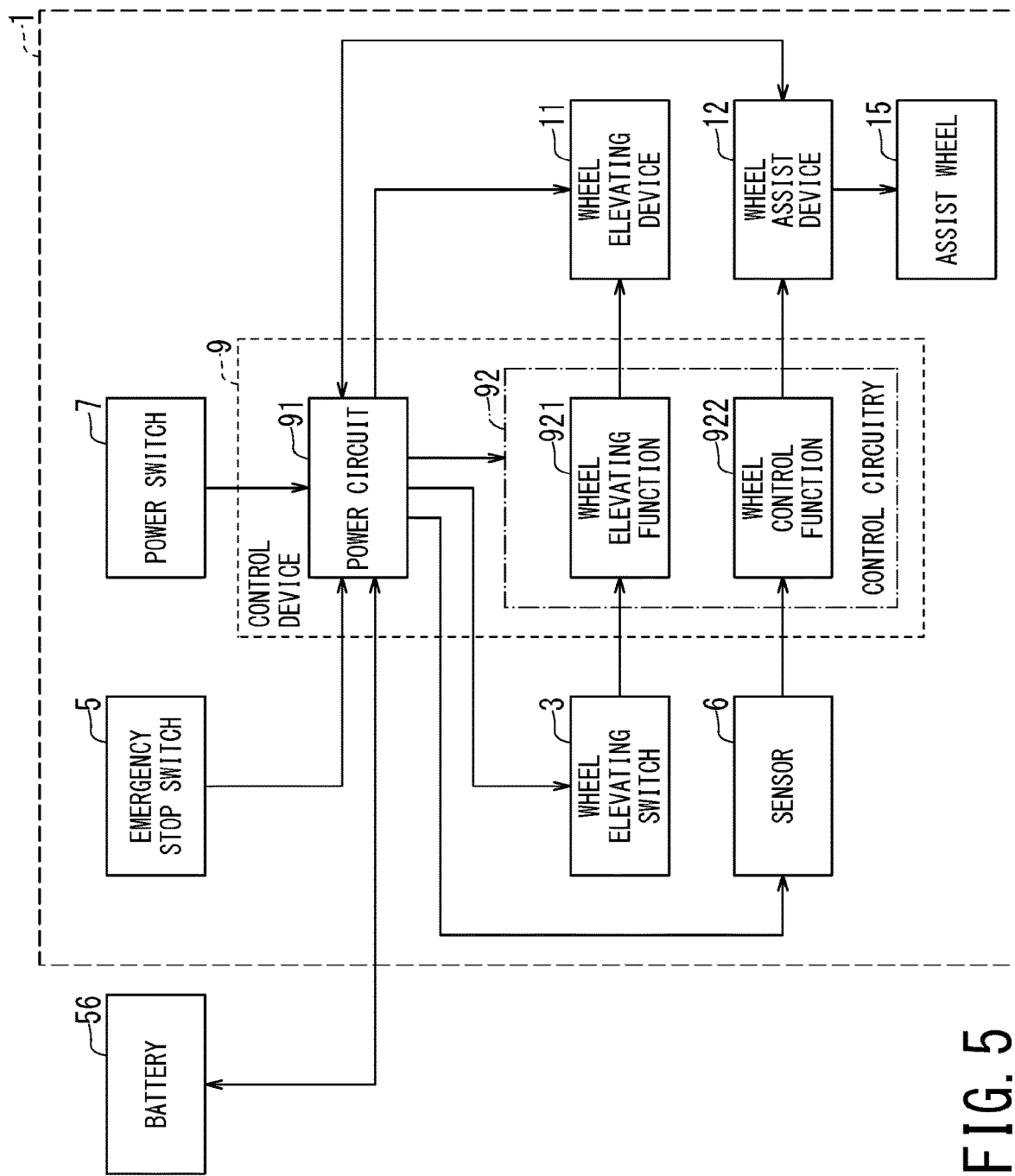
FIG. 5 is a block diagram showing an example of a functional configuration of the ultrasonic diagnostic apparatus according to the embodiment.

FIG. 5 is a block diagram showing an example of a functional configuration of the ultrasonic diagnostic apparatus 100 according to the embodiment. As shown in FIG. 5, the control device 9 has a power circuit 91 and a control circuitry 92.

The power circuit 91 includes a processor and a memory. The processor of the power circuit 91 controls the power supply to each component of the movement assist unit 1 such as the wheel assist device 12 by executing the program stored in the memory.

The power circuit 91 may charge the battery 56 with the regenerative power of the wheel assist device 12. Further, the power circuit 91 may stop or limit supplying the power to each component of the movement assist unit 1 when the amount of the electricity stored in the battery 56 falls below a predetermined threshold value.

When the power circuit 91 receives an emergency stop signal from the emergency stop switch 5, the power circuit 91 stops the power supply to the wheel assist device 12.

Each component of the ultrasonic diagnostic apparatus 100 may be configured such that an emergency stop can be performed even if the emergency stop switch 5 is not directly pressed by the user. For example, when an obstacle is detected by the obstacle detection sensor provided in the forward surface or the lower part of the forward side of the ultrasonic diagnostic apparatus 100, the power circuit 91 may stop the power supply to the wheel assist device 12. For the user who is on the rearward side and operates the rear handlebar 2, the forward and the lower part of the forward of the ultrasonic diagnostic apparatus 100 can be blind spots. Therefore, a sensor for detecting an obstacle may be provided at such a position, and the ultrasonic diagnostic apparatus 100 may be automatically stopped so as not to collide with the obstacle and not to catch the obstacle in the forward lower part of the ultrasonic diagnostic apparatus 100. The sensor for detecting an obstacle may be turned on only when the assist wheel assists the movement of the ultrasonic diagnostic apparatus 100.

The control circuitry 92 includes a processor and a memory. The wheel elevating function 921 and the wheel control function 922 are realized by the processor of the control circuitry 92 executing the program stored in the memory. At least one of the processor and the memory included in the control circuitry 92 may be shared with the processor and the memory included in the power circuit 91.

The wheel control function 922 controls the wheel assist device 12 according to the output signal of the sensor 6. The wheel control function 922 may control the wheel assist device 12 according to the output signal of the sensor 6 according to the load toward the forward-rearward direction on the rear handlebar 2 detected by the sensor 6. When the user operates the rear handlebar 2 forward, the wheel control function 922 controls the wheel assist device 12 so as to assist the forward travel of the ultrasonic diagnostic apparatus 100, and controls the rotation direction of the assist wheel 15. On the contrary, when the user operates the rear handlebar 2 rearward, the wheel control function 922 controls the wheel assist device 12 so as to assist the reverse travel of the ultrasonic diagnostic apparatus 100, and controls the rotation direction of the assist wheel 15. Further, the wheel control function 922 controls the wheel assist device 12 such that the rotation speed of the assist wheel 15 changes according to the force by which the user operates the rear handlebar 2 forward or rearward.

The wheel elevating function 921 receives the signal output from the wheel elevating switch 3 and controls the wheel elevating device 11 to raise and lower the assist wheel 15, thereby controlling switching between grounded and ungrounded of the assist wheel 15.

For example, when the rear handlebar 2 is gripped by the user, the wheel elevating switch 3 is pressed, and the wheel elevating function 921 receives the lowering signal. Upon receiving the lowering signal, the wheel elevating function 921 controls the wheel elevating device 11 such that the assist wheel 15 is grounded to the floor. Meanwhile, when the user releases the rear handlebar 2 (when the rear handlebar 2 is not gripped by the user), the wheel elevating switch 3 is released, and the wheel elevating function 921 receives the raising signal. When the wheel elevating function 921 receives the raising signal, the wheel elevating function 921 controls the wheel elevating device 11 such that the assist wheel 15 moves off the floor (becomes ungrounded).

Figure 6A:
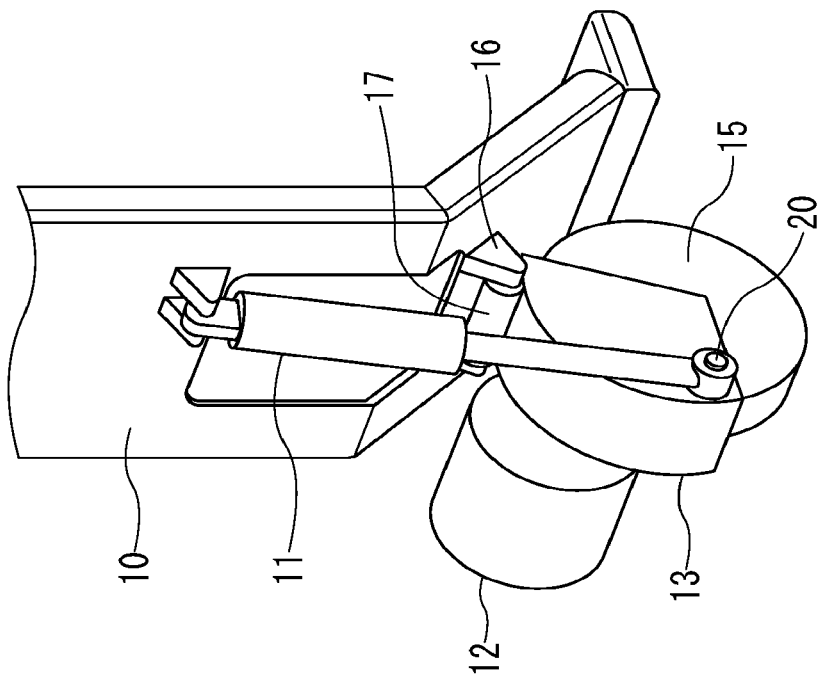
FIG. 6A is a perspective view of a mounting portion of the assist wheel of the movement assist unit.
Figure 6B:
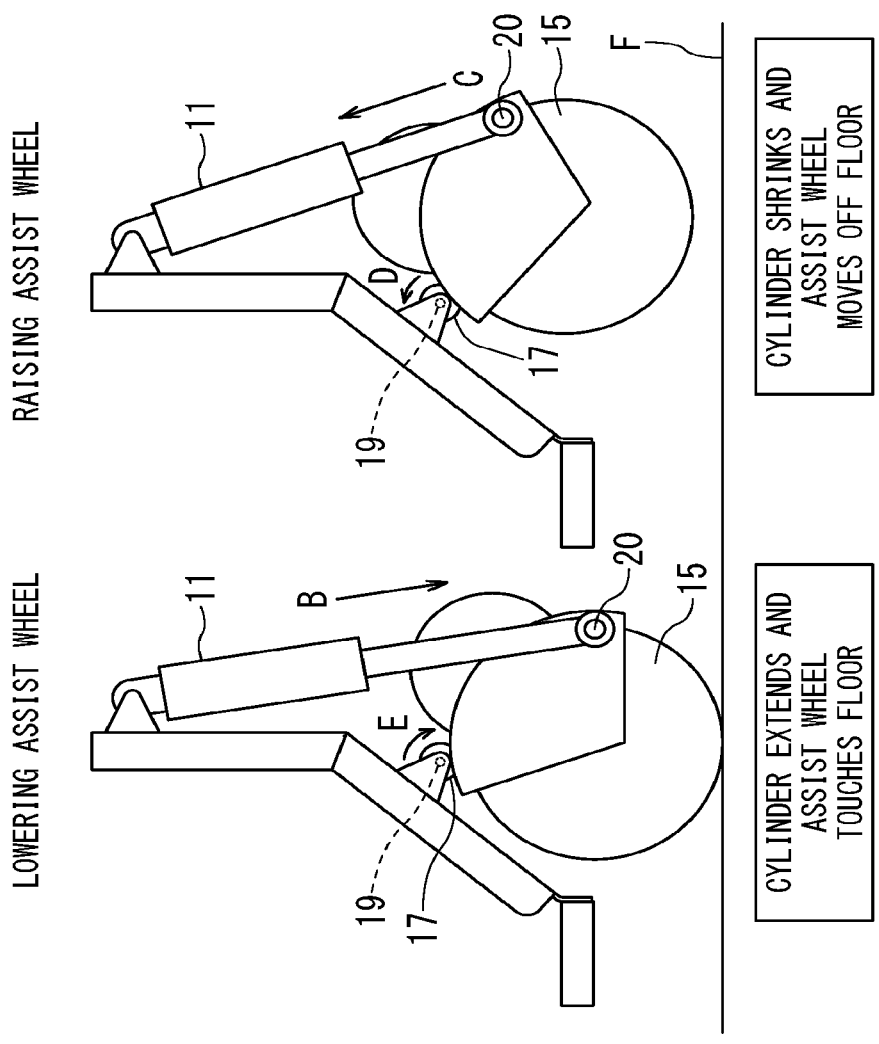
FIG. 6B is an explanatory view showing an example of the operation of the wheel elevating device for raising and lowering the assist wheel.

FIG. 6A is a perspective view of a mounting portion of the assist wheel 15 of the movement assist unit 1. FIG. 6B is an explanatory view showing an example of the operation of the wheel elevating device 11 for raising and lowering the assist wheel 15.

As shown in FIG. 6A, the arc-shaped wheel cover 13 covers a part of the assist wheel 15 such that the center of the circle formed by the arc of the wheel cover 13 and the rotation axis of the assist wheel 15 are coaxial. Further, the holding member 10 has a protruding portion 16 for holding the wheel cover 13. Two protruding portion 16 are provided so as to sandwich the hook portion 17 provided on the wheel cover 13, and protrusions are provided at the respective tips of the two protruding portions 16 so as to face each other. The pair of protrusions sandwich the hook portion 17 of the wheel cover 13 to hold the assist wheel 15. A shaft formed by the pair of protrusions is used as a support shaft 19. The assist wheel 15 is rotatably attached around the support shaft 19.

As shown in FIG. 6A, the upper part of the wheel elevating device 11 is attached to the holding member 10, and the lower part of the wheel elevating device 11 is attached to the protrusion 20 provided on the wheel cover 13. The wheel elevating device 11 includes, for example, an electric cylinder 11 and expands and shrinks (contracts) according to the control of the wheel control function 922 to switch between grounded and ungrounded of the assist wheel 15.

Specifically, when the electric cylinder 11 shrinks and the wheel cover 13 is lifted together with the protrusion 20 provided on the wheel cover 13, the hook portion 17 of the wheel cover 13 rotates around the support shaft 19. As a result, the assist wheel 15 also rotates around the support shaft 19 together with the wheel cover 13. On the contrary, when the electric cylinder 11 extracts and the wheel cover 13 is pushed down together with the protrusion 20 provided on the wheel cover 13, the hook portion 17 of the wheel cover 13 rotates around the support shaft 19. As a result, the assist wheel 15 also rotates around the support shaft 19 together with the wheel cover 13.

As shown on the right side of FIG. 6B, when the electric cylinder 11 contracts in the direction of arrow C, the protrusion 20 provided on the wheel cover 13 is pulled up in the direction of arrow C. At the same time, the hook portion 17 of the wheel cover 13 rotates about the support shaft 19 in the direction of the arrow D. Thus, the assist wheel 15 rotates around the support shaft 19 provided outside the assist wheel 15, and the assist wheel 15 is ungrounded from the floor F.

Meanwhile, as shown on the left side of FIG. 6B, when the electric cylinder 11 extends in the direction of arrow B, the protrusion 20 provided on the wheel cover 13 is pushed down in the direction of arrow B. At the same time, the hook portion 17 of the wheel cover 13 rotates about the support shaft 19 in the direction of the arrow E. Thus, the assist wheel 15 rotates around the support shaft 19 provided outside the assist wheel 15, and the assist wheel 15 touches the floor F.

The elevating mechanism of the assist wheel 15 is not limited to the example shown in FIGS. 6A and 6B. The assist wheel 15 may be provided at the tip of the electric cylinder 11 mounted perpendicularly to the floor F on the floor side via the wheel cover 13. In this case, the assist wheel 15 may move up and down in the direction perpendicular to the floor F according to the expansion and contraction of the electric cylinder 11, whereby the assist wheel 15 may be switched between grounded and ungrounded.

(2) Operation

Next, an example of the operation of the ultrasonic diagnostic apparatus 100 according to the embodiment will be described.

Figure 7:
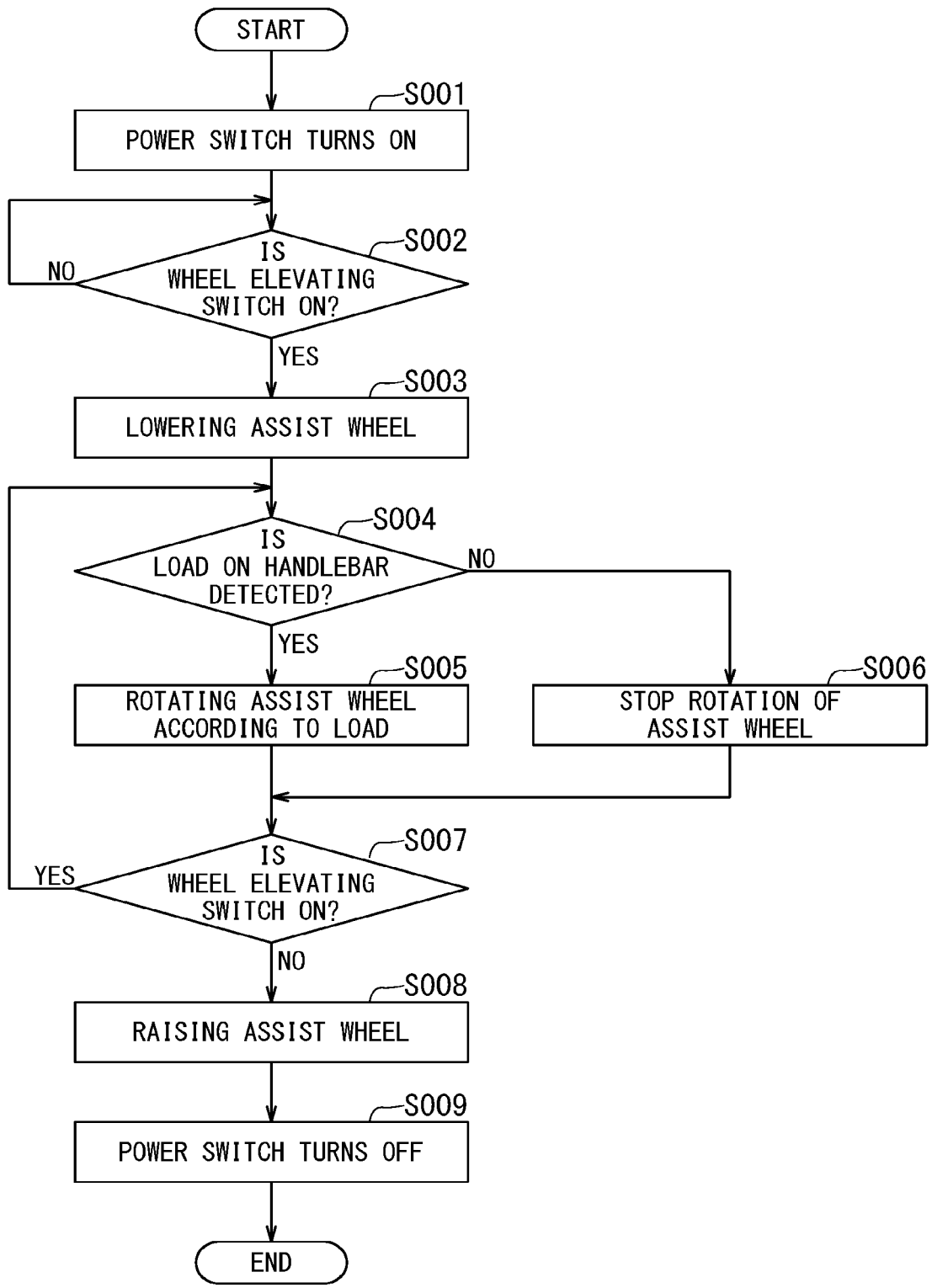
FIG. 7 is a flowchart showing an example of the operation of the ultrasonic diagnostic apparatus according to the embodiment.

FIG. 7 is a flowchart showing an example of the operation of the ultrasonic diagnostic apparatus 100 according to the embodiment. A reference character with "S" followed by a number in FIG. 7 denotes each step of the flowchart. In the flowchart of FIG. 7, a case where the ultrasonic diagnostic apparatus 100 is moved from one room to another room will be described as an example.

In step S001, the power switch 8 is pressed, and power from the battery 56 is supplied to each component of the movement assist unit 1 via the power circuit 91.

In step S002, the wheel elevating function 921 determines whether or not the wheel elevating switch 3 is pressed. For example, when the user grips the rear handlebar 2, the wheel elevating switch 3 provided on the rear handlebar 2 is pressed at the same time. When the wheel elevating switch 3 is pressed by the user, the wheel elevating switch 3 outputs a lowering signal. When the wheel elevating function 921 receives the lowering signal, the process proceeds to YES in step S002 and step S003. When the wheel elevating switch 3 is not pressed (released), the process proceeds to NO in step S002 and returns to step S002.

In step S003, the wheel elevating function 921 controls the wheel elevating device 11 to lower the assist wheel 15 and bring it to the ground.

The wheel elevating switch 3 may output a signal only once when it is pressed (released), or may output a signal during it is pressed (released). Further, the wheel elevating function 921 may store the current grounded or ungrounded states of the assist wheel 15 in the memory, and may control the wheel elevating device 11 by receiving a signal for changing the state of the assist wheel 15. The wheel elevating function 921 may lower the assist wheel 15 according to the lowering signal received while the assist wheel 15 is ungrounded.

In step S004, the sensor 6 detects the load generated by the user operating the rear handlebar 2. When the sensor 6 detects the load on the rear handlebar 2, the process proceeds to YES in step S004 and step S005. When the load on the rear handlebar 2 is not detected by the sensor 6, the process proceeds to NO in step S004 and step S006. The operations of step S004 and step S005 are repeated until the process proceeds to NO in step S004.

In step S005, the wheel control function 922 rotates the assist wheel 15 according to the output of the sensor 6. When the sensor 6 detects that the rear handlebar 2 is operated in the forward travel direction, the wheel control function 922 controls the wheel assist device 12 such that the assist wheel 15 rotates in the forward travel direction. When the sensor 6 detects that the rear handlebar 2 is operated in the reverse travel direction, the wheel control function 922 controls the wheel assist device 12 such that the assist wheel 15 rotates in the reverse travel direction.

Further, the sensor 6 detects the magnitude of the load applied to the rear handlebar 2 when the user operates the rear handlebar 2, and the wheel control function 922 controls the wheel assist device to increase or decrease the rotation speed of the assist wheel 15 according to the magnitude of the load. The larger the force with which the user operates the rear handlebar 2, the larger the load detected by the sensor 6. The wheel control function 922 controls the wheel assist device such that the larger the detected load, the greater the rotation speed of the assist wheel 15.

The wheel control function 922 may drive the wheel assist device 12 only when the load on the rear handlebar 2 detected by the sensor 6 reaches a predetermined threshold value or more. In this case, the wheel control function 922 may prevent the wheel assist device 12 from being driven immediately after the sensor 6 detects a load on the rear handlebar 2, whereby the sudden start of the ultrasonic diagnostic apparatus 100 can be prevented.

The wheel control function 922 may control the wheel assist device 12 such that the rotation speed of the assist wheel 15 does not increase further when the sensor 6 detects a load equal to or higher than a certain threshold value. Further, the wheel control function 922 may calculate the running speed of the ultrasonic diagnostic apparatus 100 from the rotation speed of the assist wheel 15 and control the rotation speed of the assist wheel 15 of the ultrasonic diagnostic apparatus 100.

The wheel control function 922 may monitor the rotation speed of the assist wheel 15, and stops driving the wheel assist device 12 when the rotation speeds exceeds the predetermined threshold value. Further, the wheel control function 922 may control the wheel assist device 12 so as to drive the wheel assist device 12 again when the rotation speed falls below the predetermined threshold value. In this case, it is possible to prevent the ultrasonic diagnostic apparatus 100 from becoming too fast while traveling. Further, even when the driving of the wheel assist device 12 is stopped, the assist wheel 15 keep rotating by inertia, and thus, the power consumption of the battery 56 can be suppressed. The wheel control function 922 may keep a predetermined travelling speed of the ultrasonic diagnostic apparatus 100 by controlling the wheel assist device 12 such that the rotation speed of the assist wheel 15 does not drop too much. In this way, by controlling the rotation speed of the assist wheel 15 by the wheel control function 922, it is possible to suppress the power consumption of the battery 56 when moving between rooms, and extend the battery operating time of the ultrasonic diagnostic apparatus 100 after moving.

When the load on the rear handlebar 2 is no longer detected by the sensor 6, in step S006, the rotation of the assist wheel 15 by the wheel assist device 12 is stopped by the control of the wheel control function 922.

In step S007, the wheel elevating function 921 determines whether or not the wheel elevating switch 3 is pressed. For example, when the user releases the rear handlebar 2, the wheel elevating switch 3 provided on the rear handlebar 2 is released at the same time. When the wheel elevating switch 3 is released from the user, the wheel elevating switch 3 outputs a raising signal. When the wheel elevating function 921 receives the raising signal, the process proceeds to NO in step S007 and step S008. When the wheel elevating switch 3 is pressed, the process proceeds to YES in step S007 and returns to step S004.

In step S008, the wheel elevating function 921 controls the wheel elevating device 11 to raise the assist wheel 15 and separate it from the floor (make it ungrounded).

In step S009, when the power switch 8 is released, the power supply to each component of the movement assist unit 1 is stopped.

The description shown above is the explanation of the flowchart of FIG. 7.

When moving the ultrasonic diagnostic apparatus 100 between rooms, the user will move the ultrasonic diagnostic apparatus 100 for a relatively long distance. The wheel elevating function 921 identifies the start of movement of the ultrasonic diagnostic apparatus 100 between rooms by the user when the wheel elevating switch 3 is pressed, and automatically lowers the assist wheel 15. Further, the wheel control function 922 rotates the assist wheel 15 according to the magnitude of the load of the rear handlebar 2 to increase the propulsive force of the ultrasonic diagnostic apparatus 100. Hence, the user can easily move the ultrasonic diagnostic apparatus 100 between rooms.

Meanwhile, when the ultrasonic diagnostic apparatus 100 is moved in a room, the position of the ultrasonic diagnostic apparatus 100 is finely adjusted, for example, when the user pulls the ultrasonic diagnostic apparatus 100 to the inspection position for the user's convenience. Although the moving distance of the ultrasonic diagnostic apparatus 100 is short, it is required to efficiently move the ultrasonic diagnostic apparatus 100 in a limited space. In this case, the conventional main wheels 55a to 55d, which can turn in a small circle and move freely in the room, are useful. According to the ultrasonic diagnostic apparatus 100, the assist wheel 15 is automatically ungrounded when the movement between rooms by the user is completed. Thereby, the position of the ultrasonic diagnostic apparatus 100 can be easily adjusted in a room by the main wheels 55a to 55d as the conventional ultrasonic diagnostic apparatus.

FIG. 7 shows an example in which the assist wheel 15 is rotated to assist the movement of the ultrasonic diagnostic apparatus 100 while the load on the rear handlebar 2 is detected by the sensor 6. However, the assistance of the movement of the ultrasonic diagnostic apparatus 100 by the assist wheel 15 is not limited to the time when the load on the rear handlebar 2 is detected by the sensor 6.

For example, the rotation of the assist wheel 15 may be a predetermined period after the rotation of the assist wheel 15 starts. The wheel control function 922 may stop driving the wheel assist device 12 after the rotation of the assist wheel 15 has started and the predetermined period has elapsed.

In this case, the wheel assist device 12 is driven only at the start of movement of the ultrasonic diagnostic apparatus 100 for the predetermined period. Since a larger force is required at the start of movement than during running, the burden on the user at the start of movement can be reduced. Further, the power consumption of the battery 56 can be suppressed by stopping the driving of the wheel assist device 12 after reaching a certain speed after the movement of the ultrasonic diagnostic apparatus 100 is started. Further, when the driving of the wheel assist device 12 is stopped during traveling after the start of movement, the battery 56 may be charged by the regenerative power generated by the wheel assist device 12. When the drive of the wheel assist device 12 is stopped during traveling, the wheel elevating function 921 may control the wheel elevating device 11 so as to raise the assist wheel 15 and unground it.

Further, the ultrasonic diagnostic apparatus 100 may be provided with a speed sensor, and when the speed of the ultrasonic diagnostic apparatus 100 is equal to or less than a predetermined speed, the wheel control function 922 may control the wheel assist device 12 such that the assist wheel 15 rotates until the speed becomes equal to or higher than the predetermined speed. In this case, the wheel assist device 12 is driven only while the movement speed is slow, e.g., at the start of movement. When moving between rooms, it is assumed that the ultrasonic diagnostic apparatus 100 is temporarily stopped and then moved again when getting on and off the elevator. Therefore, the wheel control function 922 may automatically determine the start of movement based on the signal from the speed sensor and control the rotation of the assist wheel 15.

Further, when the amount of electricity stored in the battery 56 falls below the predetermined threshold value, the wheel control function 922 may drive the wheel assist device 12 only at the start of movement in order to minimize the electric power used by the movement assist unit 1. Further, even while moving between rooms, when the amount of electricity stored in the battery 56 falls below the predetermined threshold value, the power circuit 91 may stop supplying power to the wheel assist device 12. Further, when the amount of electricity stored in the battery 56 falls below the predetermined threshold value, the wheel control function 922 may be controlled such that the rotation speed of the wheel assist device 12 does not exceeds the predetermined threshold value in order to suppress the power consumption of the battery 56.

Further, the power circuit 91 may measure the amount of electricity stored in the battery 56, and a display indicating the stored amount may be provided at a position visible to the user on the surface of the control device 9 or the surface of the battery 56. Further, based on the amount of electricity stored in the battery 56, the display may display the image indicating whether or not the movement assist unit 1 can be used, and/or the image indicating the operation time of the movement assist unit 1 and the operation time of the ultrasonic diagnostic apparatus 100.

In FIG. 7, the example of the ultrasonic diagnostic apparatus 100 is described in which the wheel elevating switch 3 is pressed at the same time as the user grips the rear handlebar 2 and then the assist wheel 15 is automatically grounded. However, the wheel elevating switch 3 may be pressed by the user at any time. For example, when climbing a slope, the user may manually press the wheel elevating switch 3 before reaching the slope to ground the assist wheel 15. In this way, the assist wheel 15 may be lowered at a timing desired by the user, and the assist function may be used.

According to at least one embodiment described above, the ultrasonic diagnostic apparatus can be easily moved.

The term "processor" used in the explanation in the above-described embodiments, for instance, refer to circuitry such as CPUs (Central Processing Units), GPUs (Graphics Processing Units), or application specific integrated circuits (ASICs), programmable logic devices including SPLDs (Simple Programmable Logic Devices), CPLDs (Complex Programmable Logic Devices), and FPGAs (Field Programmable Gate Arrays), and the like. When the processor is a CPU, the processor realizes a function by reading and executing a program stored in a memory. When the processor is an ASIC, instead of storing the program in the memory, the function corresponding to the program is directly incorporated as a logic circuit in the circuit of the processor. In this case, the processor realizes various functions by hardware processing that reads and executes a program embedded in the circuit. Alternatively, the processor can also realize various functions by combining software processing and hardware processing.

Further, the processor may be composed of a single circuit or a combination of a plurality of independent circuits. In the latter case, a memory may be individually provided for each circuit of the plurality of circuits, or a single memory may store a program corresponding to all the functions of the plurality of circuits.

While certain embodiments have been described, these embodiments have been presented by way of example only, and are not intended to limit the scope of the inventions.

Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus, comprising:
a body configured to send and receive ultrasonic waves to generate an ultrasonic image;
a plurality of wheels configured to support and move the body;
an assist wheel electrically driven and configured to assist movement of the body;
a wheel elevating switch;
a handlebar configured to move the body, wherein the wheel elevating switch is provided on the handlebar and is configured to detect whether the handlebar is gripped by a user; and
control circuitry configured to
control switching between grounded and ungrounded states of the assist wheel to a floor by raising and lowering the assist wheel in response to a signal from the wheel elevating switch provided on the handlebar, and
ground the assist wheel when the handlebar is gripped and unground the assist wheel when the handlebar is not gripped.

2. The ultrasonic diagnostic apparatus according to claim 1, wherein the assist wheel is configured to be raised and lowered by rotating around a support shaft of the assist wheel provided outside the assist wheel.

3. The ultrasonic diagnostic apparatus according to claim 1, wherein the assist wheel is configured to be raised and lowered in a direction perpendicular to the floor.

4. The ultrasonic diagnostic apparatus according to claim 1, further comprising a holding member holding the assist wheel and the control circuitry,
wherein the holding member is detachably attached to the body.

5. The ultrasonic diagnostic apparatus according to claim 1, further comprising a detector configured to detect a load in a front-rear direction on the handlebar,
wherein the control circuitry is further configured to rotate the assist wheel according to the load in the front-rear direction on the handlebar.

6. The ultrasonic diagnostic apparatus according to claim 5, wherein the control circuitry is further configured to rotate the assist wheel for a predetermined period after the load on the handlebar is detected.

7. The ultrasonic diagnostic apparatus according to claim 1, further comprising a battery configured to supply power to both the body and an assist motor that drives the assist wheel.

8. The ultrasonic diagnostic apparatus according to claim 7, further comprising a power circuit configured to control power supply from the battery to the assist motor.

9. The ultrasonic diagnostic apparatus according to claim 8, wherein, when the assist wheel rotates while the assist motor does not rotate, the power circuit is further configured to charge the battery with a regenerative power of the assist motor.

10. The ultrasonic diagnostic apparatus according to claim 8, wherein the power circuit is further configured to stop supplying power to the assist motor when receiving an emergency stop signal.

11. The ultrasonic diagnostic apparatus according to claim 8, wherein the power circuit is further configured to stop supplying power to the assist motor when an amount of electricity stored in the battery falls below a threshold value.

12. The ultrasonic diagnostic apparatus according to claim 1, wherein
the plurality of wheels includes two front wheels and two rear wheels; and
the assist wheel is provided between the two rear wheels.

13. The ultrasonic diagnostic apparatus according to claim 1, further comprising a speed sensor configured to detect a speed of the ultrasonic diagnostic apparatus,
wherein, when the detected speed of the ultrasonic diagnostic apparatus is equal to or less than a predetermined speed, the control circuitry is further configured to control the assist wheel such that the assist wheel rotates until the speed of the ultrasonic diagnostic apparatus becomes equal to or higher than the predetermined speed.

* * * * *